United States Patent [19]

Baney et al.

[11] Patent Number: 4,965,367

[45] Date of Patent: Oct. 23, 1990

[54] PROCESS FOR PREPARATION OF SILACYCLOBUTANES

[75] Inventors: Ronald H. Baney; Carl J. Bilgrien; Lawrence D. Fiedler; Chi-long Lee, all of Midland, Mich.

[73] Assignee: Dow Corning Corporation, Midland, Mich.

[21] Appl. No.: 422,207

[22] Filed: Oct. 16, 1989

[51] Int. Cl.$^5$ .............................. C07F 7/08; C07F 7/10
[52] U.S. Cl. ...................................... 548/110; 556/406
[58] Field of Search .......................... 548/110; 556/406

[56] References Cited

U.S. PATENT DOCUMENTS

| | | | |
|---|---|---|---|
| 3,046,291 | 7/1962 | Sommer | 260/448.2 |
| 3,687,995 | 8/1972 | Jonas et al. | 260/46.5 |
| 3,694,427 | 9/1972 | Janas et al. | 260/18 S |

FOREIGN PATENT DOCUMENTS 1328514  8/1973  United Kingdom .

OTHER PUBLICATIONS

R. Bush, Ph.D. Thesis, Univ. of California at Davis, 1975; *Diss. Abstr. Int. B* 1976, 36, 5034.
Nametkin, N. S.; Vdovin, V. M.; Grinberg, P. L. *Dokl. Akad. Nauk SSSR,* 1964, 155, 849 (320).
Nametkin, N. S.; Vdovin, V. M.; Babich, E. D.; Oppengeim, V.D. *Khim. Geterotsiki Soedin.,* 1965, 455.
Nametkin, N. S.; Vdovin, J, M.; Babich, E. D. *Khim. Geterotsikl Soedin.,* 1967, 148.

*Primary Examiner*—Richard L. Raymond
*Attorney, Agent, or Firm*—Edward C. Elliott

[57] ABSTRACT

Novel silacyclobutanes useful as silylating agents and a process for their preparation are provided. The process comprises reacting a halogen substituted silacyclobutane with a silylating reagent to exchange the halogen substituents with groups on the silylating reagent. The novel compounds are of the formula

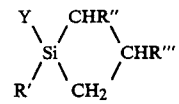

wherein R' is a monovalent substituted or unsubstituted hydrocarbon radical or Y group; R" and R"' are independently hydrogen, monovalent substituted or unsubstituted hydrocarbon radical; and Y is selected from:

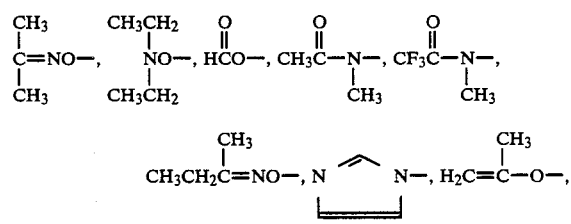

and the disubstituted silacyclobutane wherein both Y and R' are

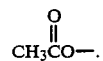

7 Claims, No Drawings

PROCESS FOR PREPARATION OF SILACYCLOBUTANES

BACKGROUND OF THE INVENTION

Several silacyclobutane monomers are known. For example, see U.S. Pat. No. 3,046,291 to Leo H. Sommer, and U.S. Pat. No. 3,687,995 to David Jonas et al. Sommer prepared his silacyclobutanes by reacting $ClCH_2CHRCH_2SiR'Cl_2$ with magnesium. Jonas et al. teach organosilicon compounds having the general formula

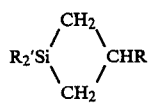

where R represents an atom or radical selected from the group consisting of hydrogen atom and alkyl radicals having less than 7 carbon atoms and R' represents alkoxy radicals having less than 5 carbon atoms or a radical of the formula $-NR''_2$, in which each R'' is a hydrogen atom ⓒr an alkyl radical. In U.S. Pat. No. 3,694,427, issued Sept. 26, 1972, Jonas et al. teach that R' can also be acyloxy radical. As an example, the reaction of 1,1-dichlorosilacyclobutane with methylorthoformate gave 1,1-dimethoxysilacyclobutane

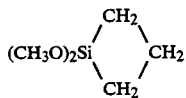

in 78% yield Further, the same compound was prepared in only 59% yield by reaction of 1,1-dichlorosilacyclobutane and methanol (Bush, R. Ph.D. Thesis, Univ. of California at Davis, 1975; *Diss. Abstr. Int. B* 1976, 36, 5034). Similarly, the reaction of 1-chloro-1-methyl-silacyclobutane and acetic anhydride gave 1-acetoxy-1-methyl-silacyclobutane

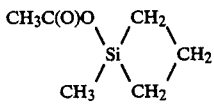

in 48% yield (Nametkin, N. S.; Vdovin, V. M.; Grinberg, P. L. *Dokl. Akad. Nauk SSSR.* 1964, 155, 849 [320]) Silacyclobutane silazanes have been prepared by metathesis reaction with formation of alkali metal salt or condensation reaction with formation of HCl (Nametkin, N. S.; Vdovin, V. M.; Babich, E. D.; Oppengeim, V. D. *Khim. Geterotsikl. Soedin.*, 1965 455) and British Patent No. 1,328,514 to Bush et al. These reactions generally give less than quantitative yields and require additional processing steps in comparison to the invention process. The invention process also provides novel compounds. See also Nametkin, N.S.; Vdovin, J. M.; Babich, E. D. *Khim. Geterotsikl. Soedin.*, 1967, 148.

Transsilylation of silazanes is taught and transsilylation of 1-chloro-1-methylsilacyclobutane with disilazanes is shown.

BRIEF SUMMARY OF THE INVENTION

Novel silacyclobutanes, useful as silylating agents, and a process for their preparation as well as for the preparation of many prior art compounds, are provided. The process comprises reacting a halogen substituted silacyclobutane with a silylating reagent to exchange the halogen substituents with groups on the silylating reagent.

DETAILED DESCRIPTION OF THE INVENTION

This invention comprises a process for preparing a silacyclobutane of the formula

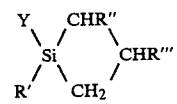

in accordance with the reaction

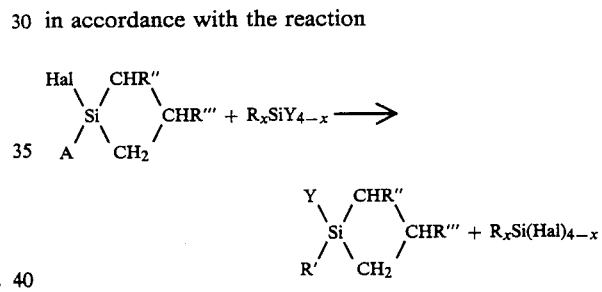

wherein A is a monovalent substituted or unsubstituted hydrocarbon radical, or halogen; Hal is a halogen; R is a monovalent substituted or unsubstituted hydrocarbon radical; R' is a monovalent substituted or unsubstituted hydrocarbon radical if A is a monovalent substituted or unsubstituted hydrocarbon radical; R' is a Y group if A is halogen; R'' and R''' are independently hydrogen, monovalent substituted or unsubstituted hydrocarbon radical; Y is a monovalent group having nitrogen or oxygen atom which bonds to the silicon atom of the silacyclobutane; and x is an integer of from 0 through 3.

Exemplary of suitable monovalent radicals for R, R', R'', and R''' are hydrogen, hydrocarbons, and substituted hydrocarbons. Thus, for example, R, R', R'', and R''' can be alkyl such as methyl, ethyl, propyl or octadecyl; substituted alkyl such as aminopropyl or thiopropyl; haloalkyl such as chloropropyl; aryl such as phenyl, xenyl or naphthyl; alkaryl such as tolyl or xylyl; aralkyl such as benzyl; unsaturated alkenyl such as vinyl, propenyl, or hexenyl; or unsaturated alkynyl such as acetylenyl or propynyl. R is preferably methyl, ethyl, vinyl, or hydrogen, and most preferably methyl. R' can be Y, which is selected from , may be
Additionally both Y and R' may be

Alkyl groups shown as CH$_3$ in these formulations for Y may be replaced by other monovalent hydrocarbon radicals. R" and R''' are preferably hydrogen or methyl. The cyclobutane ring may be substituted or unsubstituted. In either case, the nomenclature used in this application will be "silacyclobutane".

The following halogenated silacyclobutanes are prepared using conventional Grignard reaction conditions. The 1,1-dichlorosilacyclobutane is prepared from 3-chloropropyltrichlorosilane and magnesium. The 1-chloro-1-methyl-silacyclobutane is prepared from 3-chloropropylmethyldichlorosilane and magnesium. The 1,2-dimethyl-1-chlorosilacyclobutane is prepared from methyl(3-chloro-3-methylpropyl)dichlorosilane and magnesium. The 1,1-dichloro-3-methylsilacyclobutane is prepared from (3-chloro2-methylpropyl)trichlorosilane and magnesium. The desired product is obtained to some degree regardless of the ratio of silane to magnesium employed. For efficiency of operation and best yields, however, it is preferred to use about an equimolar ratio. It is also best to conduct the reaction in the presence of an inert solvent to aid in establishing contact between the reactants and as a suspension medium for the by-product MgCl$_2$. Conventional anhydrous solvents such as the hydrocarbon ethers, including cyclic ethers such as tetrahydrofuran, can all be used.

The starting organofunctional silane, R$_x$SiY$_{4-x}$, can be prepared by conventional routes. For example, trimethylsilylacetate is prepared by reaction of trimethylchlorosilane with acetic acid, acetic anhydride, or sodium acetate. N-methyl-N-(dimethylvinylsilyl)acetamide is prepared by reaction of dimethylvinylchlorosilane with the sodium salt of N-methyl- acetamide. N-trimethylsilyl-N-methyltrifluoroacetamide is prepared by reaction of trimethylchlorosilane and the sodium salt of N-methyltrifluoroacetamide. Dimethylvinylsilylformate is prepared by reaction of dimethylvinylchlorosilane with sodium formate. Methylvinylbis(methylethylketoximo)silane is prepared from the reaction of methylvinyldichlorosilane and methylethylketoxime. Methylvinylbis(diethylaminoxy)silane is prepared from methylvinyldichlorosilane and diethylhydroxylamine. N-trimethylsilylimidazole is prepared from trimethylchlorosilane and the sodium salt of imadazole.

The novel reaction described above for preparing the organofunctional silacyclobutane is efficient and quantitative and can be conducted at a mild temperature between about −50° C. and about 100° C., generally without a solvent. Typical solvents can be employed, however, such as toluene, tetrahydrofuran, benzene, chloroform, or methylene chloride. The preferred ratio of silacyclobutane to silylating agent is such that the ratio of halogen to Y group is 1 to 1, but other ratios could be used if desired. When R is a low molecular weight group such as methyl or vinyl, R$_x$Si(Hal)$_{4-x}$ is the most volatile species of the reaction, allowing it to be removed by vacuum to drive the reaction to the desired product. No heating, catalyst or purification steps are necessary. The organofunctional silacyclobutane product may be isolated without distillation by removal of the chlorosilane by-product using reduced pressure, heat or both. Alternatively, the organofunctional silacyclobutane product can be recovered by distillation.

Novel compounds that can be prepared by the process of the invention are represented by the formula

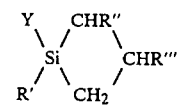

wherein R' is a monovalent substituted or unsubstituted hydrocarbon radical or Y group; R" and R''' are independently hydrogen, monovalent substituted or unsubstituted hydrocarbon radical; and Y is selected from:

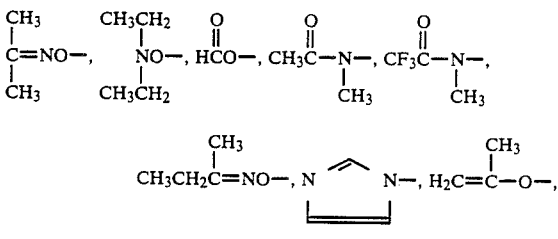

and the disubstituted silacyclobutane wherein both Y and R' are

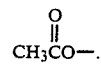

Typical uses for the organofunctional silacyclobutanes of the invention are (a) chain extending hydroxy endblocked polydiorganosiloxanes such as HO(R$_2$SiO)$_n$H using compounds of the invention having the formula:

where n is an integer equal to or greater than 2, R' is a Y and the other substituents are as previously defined; (b) endcapping silanol terminated polydiorganosiloxanes using compounds of the invention wherein R' is a monovalent substituted or unsubstituted hydrocarbon radical; (c) functionalizing siloxane resins containing silanol radicals by reacting the SiOH with the silacyclobutane Y group; and (d) functionalizing silica or glass surfaces by similarly introducing the silacyclobutane group.

The following examples will serve to illustrate the silacyclobutanes of this invention and the claimed method of their manufacture. These examples are included for illustrative purposes only and should not be construed as limiting the invention, which is properly set forth in the appended claims. All parts and percentages in said examples and elsewhere in the specification and claims are by weight unless otherwise indicated.

EXAMPLE 1

1,1-Diacetoxysilacyclobutane

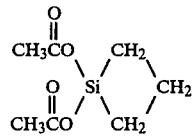

To 30.0 g trimethylsilylacetate was added 16.0 g 1,1-dichlorosilacyclobutane. The reactants were stirred for one hour at 25 ° C. and fractional distillation performed on the reaction mixture. The title compound was isolated as a clear, colorless fluid. The yield was 14.6 g (81.4%). The structure of the product was confirmed by mass spectroscopy and nuclear magnetic resonance spectroscopy (NMR).

EXAMPLE 2

1,1-Bis((N-methyl)acetamido)silacyclobutane

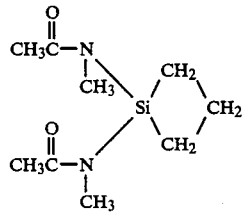

An admixture of 20.7 g of N-methyl-N-(dimethylvinylsilyl)acetamide and 9.27 g of 1,1-dichlorosilacyclobutane was prepared, which generated a noticeable exotherm. Immediate fractional distillation gave a clear pale yellow liquid. The boiling point was 111°-112° C. at 0.1 mm Hg. The yield was 9.97 g (92%). The product was identified by NMR and mass spectroscopy. Within 24 hours, the distilled product turned dark red and solidified. The crystalline product reacts violently with water and is very soluble in chloroform, tetrahydrofuran, and toluene.

EXAMPLE 3

1,1-Bis((N-methyl)trifluoroacetamido)silacyclobutane
t,110

An admixture of 0.88 g N-trimethylsilyl-N-methyl trifluoroacetamide and 0.35 g 1,1-dichlorosilacyclobutane immediately gave a fuming clear mixture. The product was identified by mass spectroscopy.

EXAMPLE 4

1,1-Diformatosilacyclobutane

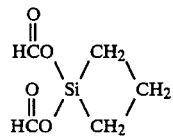

An admixture of 0.56 g 1,1-dichlorosilacyclobutane and 1.01 g dimethylvinylsilylformate gave a clear mixture with a mild exotherm. The product was identified by mass spectroscopy.

EXAMPLE 5

1-Acetoxy-1-methylsilacyclobutane

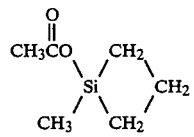

An admixture of 19.9 g 1-chloro-1-methylsilacyclobutane and 26.0 g trimethylsilylacetate gave a clear solution. By-product trimethylchlorosilane was immediately distilled over at room temperature and the solution allowed to cool. The title compound was distilled at reduced pressure. The boiling point was 90°-93.5° C. at 108 mm Hg. The yield was 17.1 g (77%). The product Was identified by NMR and mass spectroscopy.

EXAMPLE 6

1-Methyl-1-(N-methylacetamido)silacyclobutane

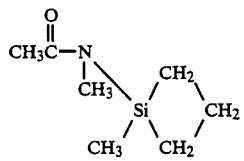

To 30.02 g 1-chloro-1-methylsilacyclobutane was added 36.10 g N-methyl-N-(trimethylsilyl)acetamide. The reaction products were fractionally distilled. The title compound was isolated as a clear, colorless fluid with a boiling point of 68°-76° C. at 3.6 mm Hg. The yield was 31.56 g (86%). The product was identified by NMR and mass spectroscopy.

EXAMPLE 7

1,1-Bis(methylethylketoximo)silacyclobutane

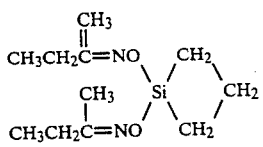

When, in accordance with the general procedure of Example 1, 1,1-dichlorosilacyclobutane and methylvinylbis(methylethylketoximo)silane are reacted together it is predicted that the title compound is formed.

EXAMPLE 8

1-Methyl-1-(methylethylketoximo)silacyclobutane

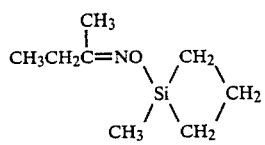

In accordance with the general procedure of Example 1, when 1-chloro-1-methylsilacyclobutane and methylvinyl-bis(methylethylketoximo)silane are reacted it is predicted that the title compound is formed.

EXAMPLE 9

1,1-Bis(diethylaminoxy)silacyclobutane

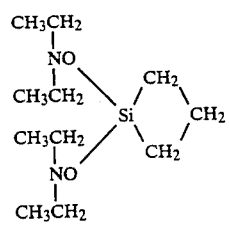

In accordance with the general procedure of Example 1, when 1,1-dichlorosilacyclobutane and methylvinylbis(diethylaminoxy)silane are reacted it is predicted that the title compound is formed.

EXAMPLE 10

1-Methyl-1-(diethylaminoxy)silacyclobutane

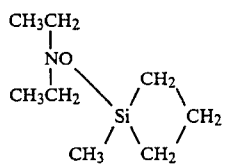

In accordance with the general procedure of Example 1, when 1-chloro-1-methylsilacyclobutane and methylvinylbis(diethylaminoxy)silane are reacted it is predicted that the title compound is formed.

EXAMPLE 11

1,1-Bis(N-imidazolato)silacyclobutane

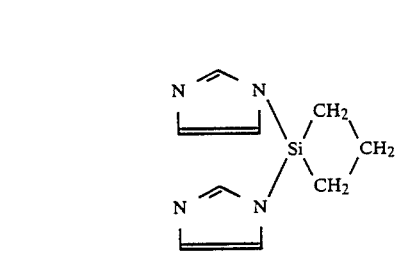

In accordance with the general procedure of Example 1 when 1,1-dichlorosilacyclobutane and N-trimethylsilylimidazole are reacted it is predicted that the title compound is formed.

EXAMPLE 12

1-Methyl-1-(N-imidazolato)silacyclobutane

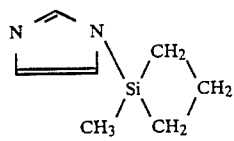

In accordance with the general procedure of Example 1, when 1-chloro-1-methylsilacyclobutane and N-trimethylsilylimidazole are reacted it is predicted that the title compound is formed.

EXAMPLE 13

1,2-Dimethyl-1-(N-methylacetamido)silacyclobutane

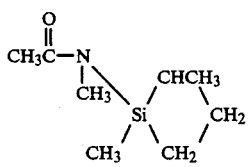

In accordance with the general procedure of Example 1, when 1-chloro-1,2dimethylsilacyclobutane and N-methyl-N-(trimethylsilyl)acetamide are reacted it is predicted that the title compound is obtained.

EXAMPLE 14

1,1-Diacetoxy-3-methylsilacyclobutane

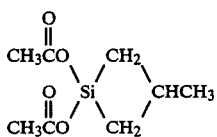

In accordance with the general procedure of Example 1, when 1,1-dichloro-3methylsilacyclobutane and trimethylsilylacetate are reacted it is predicted that the title compound is obtained.

EXAMPLE 15

1,1-Bis(isopropenoxy)silacyclobutane

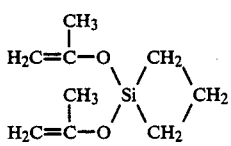

In accordance with the general procedure of Example 1, when 1,1-dichlorosilacyclobutane and isopropenoxytrimethylsilane are reacted it is predicted that the title compound is obtained.

EXAMPLE 16

1-Methyl-1-(isopropenoxy)silacyclobutane

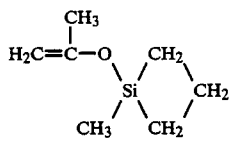

In accordance with the general procedure of Example 1, when 1,1-dichloro-3-methylsilacyclobutane and isopropenoxytrimethylsilane are reacted it is predicted that the title compound is obtained.

EXAMPLE 17

To a mixture of 75.0 g of HO(Me$_2$SiO)$_x$H (0.23 percent by weight hydroxyl radical), 3.16 g of triethylamine and 10.2 g of anhydrous magnesium sulfate in 227 g diethyl ether was added 1.53 ml 1-acetoxy-1-methylsilacyclobutane. The mixture was stirred 48 hours, filtered and stripped to 73° C. at 0.6 mm Hg to give 73.5 g of clear colorless polymer.

EXAMPLE 18

To a mixture of 152.3 g HO(Me$_2$SiO)$_x$H (about 0.14 percent by weight hydroxyl radical, Mw of about 50,000 and Mn of about 24,000) and 15.3 g anhydrous magnesium sulfate in 352g diethyl ether was added a solution of 0.197 g 1-acetoxy-1-methylsilacylobutane and 1.15 g 1,1-diacetoxysilacyclobuane in 50 ml diethyl ether. The mixture was stirred for 3 hours, filtered and stripped to 75° C. and 1.5 mm Hg to give 149.2 g clear colorless polymer. The weight average molecular weight (Mw) was 340,000 and the number average molecular weight (Mn) was 88,000 to give a Mw/Mn ratio of 3.9.

EXAMPLE 19

To a mixture of 188.8 g of the hydroxyl endblocked polymer of Example 18 and 19.8 g anhydrous magnesium sulfate in 353 g of tetrahydrofuran was added a solution of 1.60 g 1,1-bis(N-methylacetamido)silacyclobutane [CH$_3$C(O)N(CH$_3$)]$_2$Si(-CH$_2$CH$_2$CH$_2$-), and 0.26 g 1-methyl-1(N-methylacetamido) silacyclobutane in 50 ml tetrahydrofuran. The mixture was stirred for 41 hours, filtered and stripped to 75° C. at 0.8 mm Hg to give 165 g hazy viscous fluid. The fluid had a weight average molecular weight of 183,000 and a number average molecular weight of 95,000, giving a Mw/Mn ratio of 1.9.

EXAMPLE 20

To a mixture of 10.06 g of the polymer of Example 18 and 0.18 g Me$_3$SiO(Me$_2$SiO)$_3$H was stirred in 0.85 g of a 22.56 percent solution of 1,1-bis(N-methylacetamido)-silacyclobutane in chloroform to give a viscous fluid. The fluid had a Mw of 106,000, a Mn of 44,000, and a Mw/Mn ratio of 2.4.

EXAMPLE 21

When 1.72g of trimethylsilylacetamide was mixed with 0.92 g of 1,1-dichlorosilacyclobutane in 5 g of methylene chloride, a white precipitate formed. The precipitate dissolved upon shaking and slowly recrystallized as .white needles. There was no trimethylchlorosilane detected in the residual fluid, indicating that the expected reaction to form 1,1-diacetamidosilacyclobutane did not occur.

That which is claimed is:

1. A process for preparing a silacyclobutane of the formula

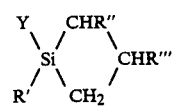

in accordance with the reaction

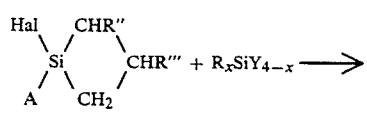

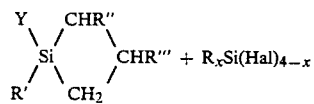

wherein A is a monovalent substituted or unsubstituted hydrocarbon radical, or halogen; Hal is a halogen; R is a monovalent substituted or unsubstituted hydrocarbon radical; R' is a monovalent substituted or unsubstituted hydrocarbon radical if A is a monovalent substituted or unsubstituted hydrocarbon radical; R' is a Y group if A is a halogen; R" and R''' are independently hydrogen, monovalent substituted or unsubstituted hydrocarbon radical; Y is a monovalent group having a nitrogen or oxygen atom which bonds to the silicon atom of the silacyclobutane; and x is an integer of from 0 through 3.

2. The process of claim 1 wherein the halogen of Hal or of A is chlorine.

3. The process of claim 1 wherein R is methyl, ethyl vinyl, or hydrogen.

4. The process of claim 1 wherein R" is methyl and R''' is hydrogen.

5. The process of claim 1 wherein both R" and R''' are hydrogen.

6. The process of claim 1 wherein R" is hydrogen and R''' is methyl.

7. The process of claim 1 wherein the molar ratio of the reactants is between about 1 SiHal group per SiY group.

* * * * *